(12) United States Patent
Chu

(10) Patent No.: US 10,085,742 B2
(45) Date of Patent: Oct. 2, 2018

(54) ADJUSTABLE DEVICE FOR DELIVERING IMPLANTS AND METHODS OF DELIVERING IMPLANTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1070 days.

(21) Appl. No.: 13/190,244

(22) Filed: Jul. 25, 2011

(65) Prior Publication Data

US 2012/0029488 A1 Feb. 2, 2012

Related U.S. Application Data

(60) Provisional application No. 61/368,782, filed on Jul. 29, 2010.

(51) Int. Cl.
| | |
|---|---|
| *A61F 2/02* | (2006.01) |
| *A61B 17/06* | (2006.01) |
| *A61B 17/00* | (2006.01) |
| *A61F 2/00* | (2006.01) |

(Continued)

(52) U.S. Cl.
CPC .. *A61B 17/06109* (2013.01); *A61B 2017/003* (2013.01); *A61B 2017/00349* (2013.01); *A61B 2017/00367* (2013.01); *A61B 2017/00805* (2013.01); *A61B 2017/00893* (2013.01); *A61F 2/0045* (2013.01); *A61F 2/0063* (2013.01);
(Continued)

(58) Field of Classification Search
CPC .... A61B 17/06109; A61B 2017/00349; A61B 17/00805; A61B 2017/06076; A61B 17/320044; A61B 2017/00367; A61B 2017/00389; A61M 5/329; A61M 2005/342; A61F 2/0045
USPC ........ 600/29, 30, 37; 128/897–899; 606/151
See application file for complete search history.

(56) References Cited

U.S. PATENT DOCUMENTS

| | | | |
|---|---|---|---|
| 6,596,001 B2 * | 7/2003 | Stormby et al. | 606/144 |
| 2005/0075660 A1 * | 4/2005 | Chu et al. | 606/190 |
| 2005/0177022 A1 * | 8/2005 | Chu et al. | 600/30 |

(Continued)

FOREIGN PATENT DOCUMENTS

| | | |
|---|---|---|
| WO | 2005048850 A2 | 6/2005 |
| WO | 2008/042433 A1 | 4/2008 |

(Continued)

OTHER PUBLICATIONS

Search Report and Written Opinion for International Application No. PCT/US2011/45397, dated Dec. 2, 2011, 15 pages.

(Continued)

*Primary Examiner* — Charles A Marmor, II
*Assistant Examiner* — Shannon McBride
(74) *Attorney, Agent, or Firm* — Brake Hughes Bellermann LLP

(57) ABSTRACT

A medical device includes an elongate member having a proximal end portion and a distal end portion. The distal end portion is configured to be inserted into a body of a patient. The elongate member is configured to be associated with a bodily implant. The distal end portion of the elongate member is configured to move from a first position to a second position such that distal end potion of the elongate member may be inserted into the body of the patient in its second position and is moved to its first position while disposed within the body of the patient.

18 Claims, 11 Drawing Sheets

(51) Int. Cl.
    *A61M 5/31*      (2006.01)
    *A61M 5/32*      (2006.01)
(52) U.S. Cl.
    CPC .... *A61F 2002/0072* (2013.01); *A61M 5/3129*
                    (2013.01); *A61M 5/329* (2013.01)

(56) References Cited

U.S. PATENT DOCUMENTS

| | | |
|---|---|---|
| 2005/0203562 A1 | 9/2005 | Palmer et al. |
| 2005/0222601 A1 | 10/2005 | Erhard et al. |
| 2008/0082105 A1* | 4/2008 | Chu ................. A61B 17/06066 606/99 |
| 2008/0132753 A1* | 6/2008 | Goddard ......................... 600/37 |
| 2009/0187222 A1 | 7/2009 | Barker |
| 2010/0023022 A1 | 1/2010 | Zeiner et al. |
| 2010/0130996 A1* | 5/2010 | Doud ................ A61M 25/0152 606/159 |

FOREIGN PATENT DOCUMENTS

| | | |
|---|---|---|
| WO | 2008042438 A2 | 4/2008 |
| WO | 2012015830 A1 | 2/2012 |

OTHER PUBLICATIONS

Communication pursuant to Article 94(3) EPC for EP Patent Application 11751980.1, dated Sep. 29, 2014, 5 pages.
Response to Communication pursuant to Article 94(3) EPC for EP Patent Application 11751980.1, filed on Jan. 22, 2015, 4 pages.
Communication pursuant to Article 94(3) EPC for EP Patent Application 11751980.1, dated May 12, 2015, 4 pages.
Response to Communication pursuant to Article 94(3) EPC for EP Patent Application 11751980.1, filed on Sep. 3, 2015, 7 pages.
Extended European Search Report for European Application No. 17182542.5, dated Nov. 20, 2017, 9 pages.

* cited by examiner ately to, U.S. Patent Application No. 61/368,782, filed Jul.
ADJUSTABLE DEVICE FOR DELIVERING IMPLANTS AND METHODS OF DELIVERING IMPLANTS

CROSS-REFERENCE TO RELATED APPLICATION

This application is a Nonprovisional of, and claims priority to, U.S. Patent Application No. 61/368,782, filed Jul. 29, 2010, entitled "ADJUSTABLE DEVICE FOR DELIVERING IMPLANTS AND METHODS OF DELIVERING IMPLANTS", which is incorporated by reference herein in its entirety.

TECHNICAL FIELD

This disclosure relates generally to medical devices and more particularly to medical devices that are configured to place or deliver implants within a body of a patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient using an insertion or delivery tool. The insertion tools used to deliver the implants within a body of a patient typically include a curved portion and a sharp needle or point at one end. Some of the insertion tools used to deliver the implants are uncontrollable and can deviate from the desired direction during the implantation process.

Accordingly, complications, such as inadvertent nerve, bladder, or uretheral punctures can occur during the implantation process. Such complications can also occur if the shape or curvature of the insertion tool is inappropriate for delivering the implant to the desired location within the body of the patient. To avoid such complications, some insertion tools use utilize a needle guide to guide the insertion tool away from organs during the implantation procedure. Additionally, in some procedures, some insertion tools must be swept (causing unintended blunt dissection with the side of the needle of the insertion tool) to direct the curved shaft of the insertion tool around or about the ischio-pubic ramus bone without causing damage to the lateral nerves or vessels.

Thus, it would be desirable to provide an insertion tool that may be used to deliver an implant to a location within a body of a patient without damaging adjacent nerves or organs.

SUMMARY

A medical device includes an elongate member having a proximal end portion and a distal end portion. The distal end portion is configured to be inserted into a body of a patient. The elongate member is configured to be associated with a bodily implant. The distal end portion of the elongate member is configured to move from a first position to a second position such that distal end potion of the elongate member may be inserted into the body of the patient in its second position and is moved to its first position while disposed within the body of the patient.

DETAILED DESCRIPTION

Figure 1:
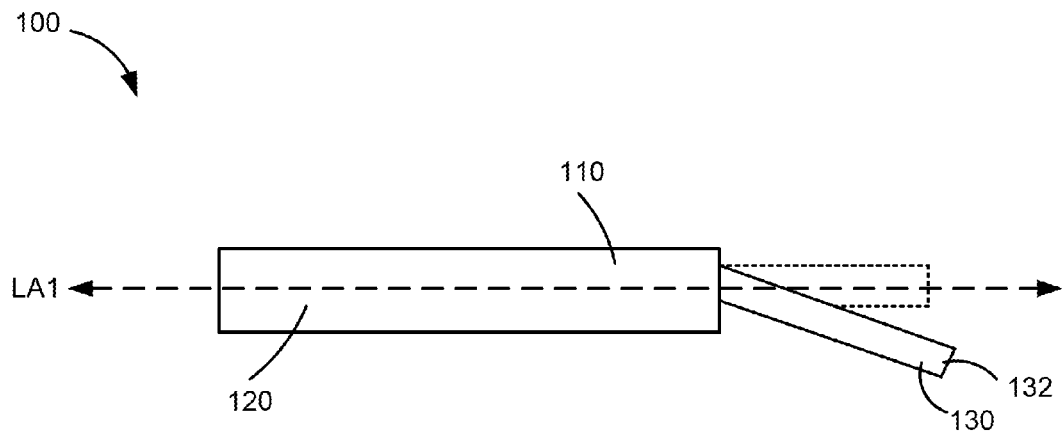
FIG. 1 is a schematic illustration of a medical device according to an embodiment.

The devices and methods described herein are generally directed to insertion or delivery tools for placing implants within a body of a patient. The implants delivered with the insertion or delivery tools include, but are not limited to, implants that are placed within a pelvic region of a patient. For example, the implants that may be placed with the disclosed insertion or delivery tools include posterior support implants, anterior support implants, and total pelvic floor repair implants. Such implants can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. The insertion tools, implants, and procedures described herein may be used in a female patient or a male patient.

In some embodiments, the disclosed insertion or delivery tool may be used to place an implant, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of an insertion tool or device as described herein refers to the end or portion of the device that is first inserted into a body of a patient during a medical procedure. The proximal end or portion is the end or portion of the device that is remains outside of the body of the patient during the insertion procedure (or if the entire device is inserted into the body of the patient during the delivery procedure, the proximal end portion is inserted into a body of the patient after the distal end or distal portion is inserted). The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that remains outside of the body of the patient or is inserted into the body after the leading end.

Various embodiments of insertion or delivery tools are described herein. The insertion or delivery tool may be used to deliver a variety of different implants into the body of a patient and only some examples of implants are described herein.

FIG. 1 is a schematic illustration of a medical device 100 according to an embodiment of the invention. The medical device 100 is configured to be used as an insertion tool or delivery tool to implant or insert a bodily implant into a body of a patient. The medical device 100 may be used to insert any type of implant into a body of a patient. In some embodiments, the medical device 100 is configured to place an implant into a pelvic region of a patient. Specifically, in some embodiments, the medical device 100 is configured to place an implant though an obturator muscle or membrane of a patient.

The medical device 100 includes an elongate member 110. The elongate member 110 includes a proximal end portion 120 and a distal end portion 130. The distal end portion 130 is moveable with respect to the proximal end portion 120. Specifically, the distal end portion 130 is configured to be placed in a first position with respect to the proximal end portion 120 and a second position (shown in dashed lines) with respect to the proximal end portion 120. In some embodiments, the distal end portion 130 is configured to move to a third position, different than the first and second positions.

In some embodiments, the distal end portion 130 includes a curved portion. The curved portion of the distal end portion 130 has a radius of curvature when the distal end portion 130 is in its first position. The curved portion of the distal end portion 130 has a radius of curvature when then the distal end portion 130 is in its second position. In some embodiments, the radius of curvature of the curved portion is greater when the distal end portion is in its second configuration than the radius of curvature of the curved portion when the distal end portion is in its first configuration.

In some embodiments, the proximal end portion 120 defines a longitudinal axis LA1. A distal tip 132 of the distal end portion 130 is disposed at a first angle with respect to the longitudinal axis LA1 when the distal end portion 130 is in it first position. The distal tip 132 of the distal end portion 130 is disposed at a second angle with respect to the longitudinal axis LA1 when the distal end portion 130 is in its second position. In some embodiments, the first angle is greater than the second angle.

In some embodiments, the distal end portion 130 is formed of a flexible material. In some such embodiments, the distal end portion 130 is configured to flex or bend from its first position to its second position. In some embodiments, the distal end portion 130 is biased to its first position (i.e., the position of a smaller radius of curvature).

In other embodiments, the distal end portion 130 is biased to its second position (i.e., the position of a larger radius of curvature). In such an embodiment, the medical device can be inserted into the body of the patient in its first position (smaller radius of curvature) and can move to its second position at a location within the body of the patient.

In some embodiments, the distal end portion 130 is formed of a biocompatible material. In some embodiments, the distal end portion 130 is formed of a stainless steel material. In other embodiments, the distal end portion 130 is formed of MP35N, nitinol, or any other material that can recover to its biased position after being disposed in its non-biased position.

In some embodiments, the distal end portion 130 can be moved from its first position to its second position by applying a force on the distal end portion 130. Once the force is removed from the distal end portion 130, the distal end portion 130 moves back to its first position. In some embodiments, the medical device 100 includes an actuator or lever that is configured to place the distal end portion 130 into its second position when activated.

The distal end portion 130 is configured to be placed within a body of a patient during an implantation procedure. In the illustrated embodiment, the distal end portion 130 is configured to be coupled to an implant to deliver the implant into the body of the patient. In some embodiments, the distal end portion 130 defines a slot (such as an L shaped slot or a T shaped slot) which is configured to receive a portion of the implant to associate or couple the implant to the medical device 100. In other embodiments, the distal end portion 130 includes a coupler, such as a hook or a loop, that is configured to be associated with a portion of an implant to couple the implant to the medical device 100.

In some embodiments, the distal tip 132 of the distal end portion 130 is configured to cut or pierce bodily tissue. For example, in some embodiments, the distal tip 132 includes a sharp portion. In other embodiments, the distal tip 132 is blunt.

The distal end portion 130 of the medical device 100 may be of any cross-sectional shape. For example, in some embodiments, the cross-sectional shape (or outer profile) of the distal end portion 130 is circular. In other embodiments, the cross-sectional shape of the distal end portion 130 is square or rectangular. In some embodiments, the distal end portion 130 has a diameter of about 16 gauge. In other embodiments, the diameter of the distal end portion 130 is greater than 16 gauge (such as 18 or 20 gauge). In yet further embodiments, the diameter of the of the distal end portion 130 is less than 16 gauge (such as 14 or 12 gauge). For example, in one embodiment, the diameter of the distal end portion is about 15 gauge. In further embodiments, the distal end portion includes a tapered portion and has a varying diameter.

In some embodiments, the medical device 100 defines a lumen that is configured to convey fluids to or from the body of the patient. For example, a lumen defined by the medical device 100 may be used to deliver medication or anesthesia to the body of the patient during the procedure to place an implant within the body of the patient. In other embodiments, the lumen may be used to help hydro-dissect the bodily tissue during an implantation procedure. The lumen defined by the medical device 100 may be of any shape or size. For example, the cross-sectional shape of the lumen may be circular, square, or rectangular.

In some embodiments, the medical device 100 may be used to insert an implant into a pelvic region of a patient. In one embodiment, the medical device 100 is coupled to or associated with an implant. The medical device 100 may then be disposed such that the distal end portion 130 is in its second position. For example, the distal end portion 130 may be placed in its second position by applying a force to the distal end portion 130. In some embodiments, a physician may apply a force to the distal end portion 130 with a hand of the physician. In other embodiments, a lever or actuator may be activated by the physician to place the distal end portion 130 into its second position.

The physician may then insert the medical device 100 into the body of the patient. In some embodiments, the medical device 100 is inserted into a pelvic region of a patient. For example, in some embodiments the medical device 100 may be used to place an implant into a body of a patient using an inside-out approach. Specifically, in some embodiments, the medical device 100 may be inserted into the pelvic region of the patient through an anterior vaginal incision.

In some embodiments, the medical device 100 is inserted into the body of the patient such that the distal tip 132 of the distal end portion 130 moves along an edge or in close proximity of an edge of a bone of the patient. As pressure is kept on the medical device 100 to move the medical device 100 within the body of the patient, the distal end portion 130 remains in its second position. In some embodiments, as the medical device 100 is moved within the body such that the distal end portion 130 moves past or away from an edge of the bone, the pressure or force on the distal end portion 130 is removed and the distal end portion 130 moves to its first position.

In some embodiments, as the distal end portion 130 moves from its second position to its first position, the distal tip 132 moves away from the nerves or organs of the patient. Thus, the medical device may be used to safely deliver an implant to a location behind or between bones of the patient. For example, in one embodiment, the medical device is configured to place an implant around a bone defining an obturator of a patient.

In some embodiments, once the medical device 100 has advanced the implant to the desired location within the body of the patient, the implant can be decoupled from the medical device 100. The medical device 100 can be withdrawn from the body of the patient to leave the implant in place within the body of the patient.

In some embodiments, the medical device 100 may be used to insert an implant into a body of the patient using an outside-in approach. Specifically, in some embodiments, the medical device 100 may be inserted into the patient through a skin incision and may be configured to extend to a location within the body of the patient. The medical device may then be coupled to an implant and retracted from the body of the patient to extend the implant into position within the body of the patient.

Figure 2:
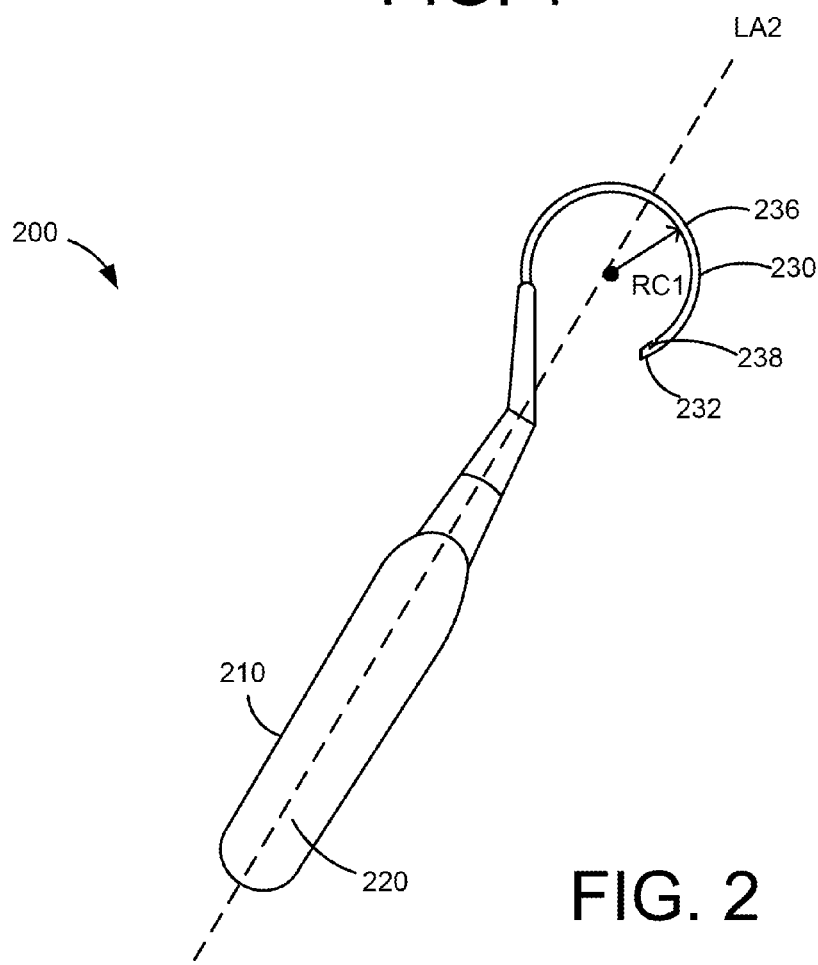
FIGS. 2-4 illustrate a medical device according to an embodiment.
Figure 4:
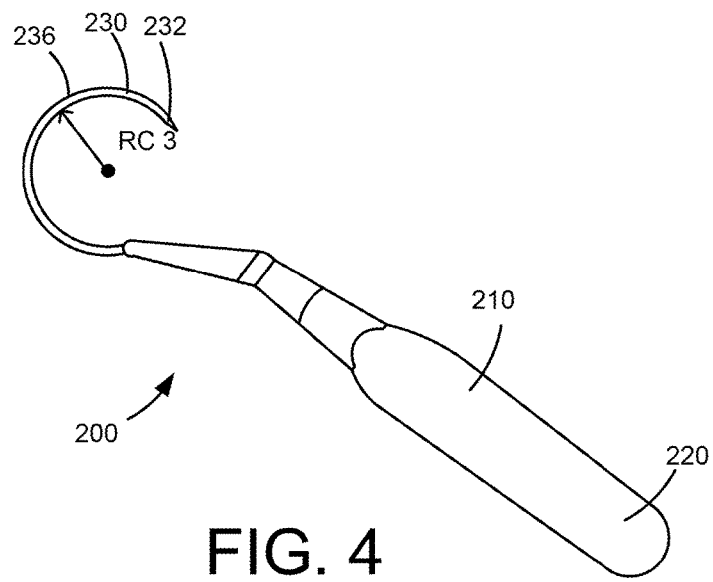
Figure 3:
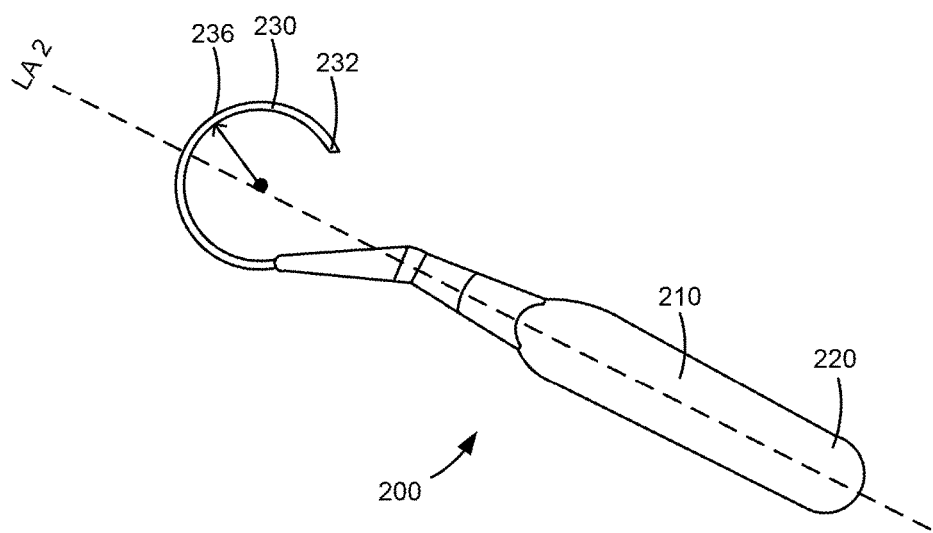

FIGS. 2-4 illustrate an embodiment of a medical device 200 according to an embodiment. The medical device 200 is configured to be used as an insertion tool or delivery tool to implant or insert a bodily implant into a body of a patient. The medical device 200 may be used to insert any type of implant into a body of a patient. In some embodiments, the medical device 200 is configured to place an implant into a pelvic region of a patient. Specifically, in some embodiments, the medical device 200 is configured to place a sling implant though an obturator muscle or obturator membrane of a patient.

The medical device 200 includes an elongate member 210. The elongate member 210 includes a proximal end portion 220 and a distal end portion 230. The distal end portion 230 is moveable with respect to the proximal end portion 220. Specifically, the distal end portion 230 is configured to be placed in a first position with respect to the proximal end portion 220 (as illustrated in FIG. 2) and a second position with respect to the proximal end portion 220 (as illustrated in FIG. 3). In the illustrated embodiment, the distal end portion 230 is also configured to move to a third position with respect to the proximal end portion 220 (as illustrated in FIG. 4). In some embodiments, the distal end portion 230 is configured to move to many different positions with respect to the proximal end portion 220.

The distal end portion 230 includes a curved portion 236. As illustrated in FIG. 2, the curved portion 236 of the distal end portion 230 has a radius of curvature RC1 when the distal end portion 230 is in its first position. In the illustrated embodiment, the radius of curvature RC1 of the curved portion 236 of the distal end portion 230 is about 1.1 inches (2.8 cm) when the distal end portion is in its first position. In other embodiments, the curved portion 236 of the distal end portion 230 has a radius of curvature that is greater or less than 1.1 inches (2.8 cm) when the distal end portion 230 is in its first position.

As illustrated in FIG. 3, the curved portion 236 of the distal end portion 230 has a radius of curvature RC2 when then the distal end portion 230 is in its second position. In the illustrated embodiment, the radius of curvature RC2 of the curved portion 236 of the distal end portion 230 is about 1.6 inches (4.1 cm) when the distal end portion 230 is in its second position. In other embodiments, the curved portion 236 of the distal end portion 230 has a radius of curvature that is greater or less than 1.6 inches (4.1 cm) when then distal end portion 230 is in its second position. In some embodiments, RC1 and RC2 do not have the same center point. Additionally, in some embodiments, the curved portion 236 does not have a uniform radius of curvature.

The radius of curvature RC2 of the curved portion 236 when the distal end portion 230 is in its second position is greater than the radius of curvature RC1 of the curved portion 236 when the distal end portion 230 is in its first position.

In the illustrated embodiment, the proximal end portion 220 defines a longitudinal axis LA2. A distal tip 232 of the distal end portion 230 is disposed at a first angle with respect to the longitudinal axis LA2 when the distal end portion 230 is in it first position. The distal tip 232 of the distal end portion 230 is disposed at a second angle with respect to the longitudinal axis LA2 when the distal end portion 230 is in its second position.

In the illustrated embodiment, the distal end portion 230 is formed of a flexible material. The distal end portion 230 is configured to flex or bend from its first position to its second position. The distal end portion 230 is biased to its first position.

The distal end portion 230 can be moved from its first position to its second position by applying a force on the distal end portion 230. Once the force is removed from the distal end portion 230, the distal end portion 230 moves back to its first position.

As illustrated in FIG. 4, the curved portion 236 of the distal end portion 230 has a radius of curvature RC3 when then the distal end portion 230 is in its third position. In the illustrated embodiment, the radius of curvature RC3 of the curved portion 236 of the distal end portion 230 is about 1.4 inches (3.6 cm) when the distal end portion 230 is in its third position. In other embodiments, the curved portion 236 of the distal end portion 230 has a radius of curvature that is greater or less than 1.4 inches (3.6 cm) when then distal end portion 230 is in its third position.

The radius of curvature RC3 of the curved portion 236 when the distal end portion 230 is in its third position is greater than the radius of curvature RC1 of the curved portion 236 when the distal end portion 230 is in its first position. The radius of curvature RC3 of the curved portion 236 when the distal end portion 230 is in its third position is less than the radius of curvature RC2 of the curved portion 236 when the distal end portion 230 is in its second position.

The distal tip 232 of the distal end portion 230 is disposed at a third angle with respect to the longitudinal axis LA2 when the distal end portion 230 is in its third position.

The distal end portion 230 is configured to be placed within a body of a patient during an implantation procedure (as discussed in more detail below). In the illustrated embodiment, the distal end portion 230 is configured to be coupled to an implant to deliver the implant into the body of the patient. The distal end portion 230 defines a slot 238, which is configured to receive a portion of the implant to associate or couple the implant to the medical device 200. In other embodiments, the distal end portion 230 includes a coupler, such as a hook or a loop, that is configured to be associated with a portion of an implant to couple the implant to the medical device 200. The distal tip 232 of the distal end portion 230 includes a sharp portion and is configured to cut or pierce bodily tissue.

In the illustrated embodiment, the distal end portion 230 of the medical device 200 has a circular cross-sectional shape (or outer profile). In some embodiments, the distal end portion 230 has a diameter of about 16 gauge.

Figure 5:
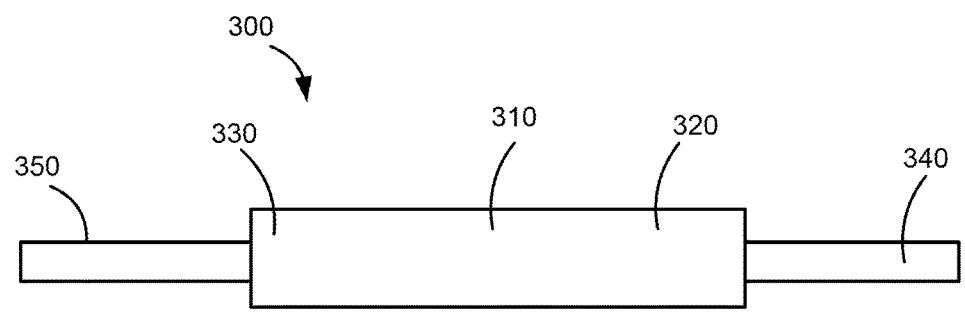
FIG. 5 is a schematic illustration of an implant according to an embodiment.

The medical device 200 may be used to insert an implant into a pelvic region of a patient. For example, an implant 300 as illustrated in FIG. 5 may be implanted into a pelvic region of a patient using the medical device 200. The implant 300 is a sling and includes a support portion 310, end portions 320 and 330, and association members 340 and 350. The support potion 310 is configured to be placed proximate a potion of the body of the patient and is configured to provide support to the portion of the body. The end portions 330 and 340 are configured to be placed into and coupled to bodily tissue to anchor the implant 300 within the body of the patient. The association members 340 and 350 are configured to associate the implant 300 to the medical device 200 during the implantation procedure.

In some embodiments, the implant 300 may be formed of any biocompatible material. In some embodiments, the implant 300 is formed of a mesh material. For example, the implant 300 may be formed of Advantage® mesh or the Polyform™ synthetic mesh, both as sold by Boston Scientific Corporation. In some embodiments, in the implant 300 may be formed of a polymer material. In some embodiments, the material of the implant 300 allows for tissue in-growth to secure the implant 300 to the bodily tissue of the patient.

In some embodiments, the implant 300 includes tangs to help retain the implant 300 in place within the body of the patient. In such embodiments, the tang or tangs are configured to engage the bodily tissue surrounding the implant 300 help retain the implant 300 in place within the body of the patient. The terms "tanged" or "tangs" as used herein mean roughened or jagged edges or areas, such as can result from cutting a woven or knit mesh material.

In one embodiment, the medical device 200 is coupled to or associated with an implant. The medical device 200 may then be disposed such that the distal end portion 230 is in its second position. For example, the distal end portion 230 may be placed in its second position by applying a force to the distal end portion 230. In some embodiments, a physician may apply a force to the distal end portion 230 with a hand of the physician.

Figure 6:
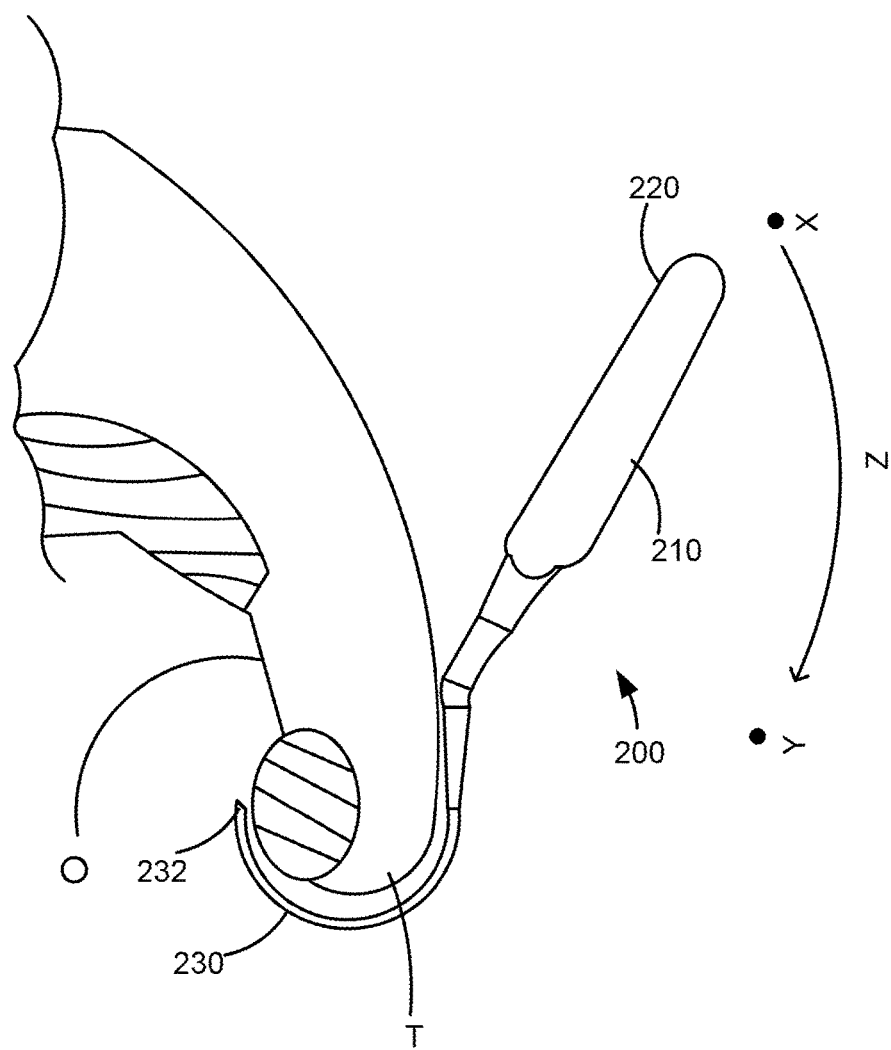
FIGS. 6-7 schematically illustrate a medical device being inserted into a body of a patient according to an embodiment.
Figure 7:
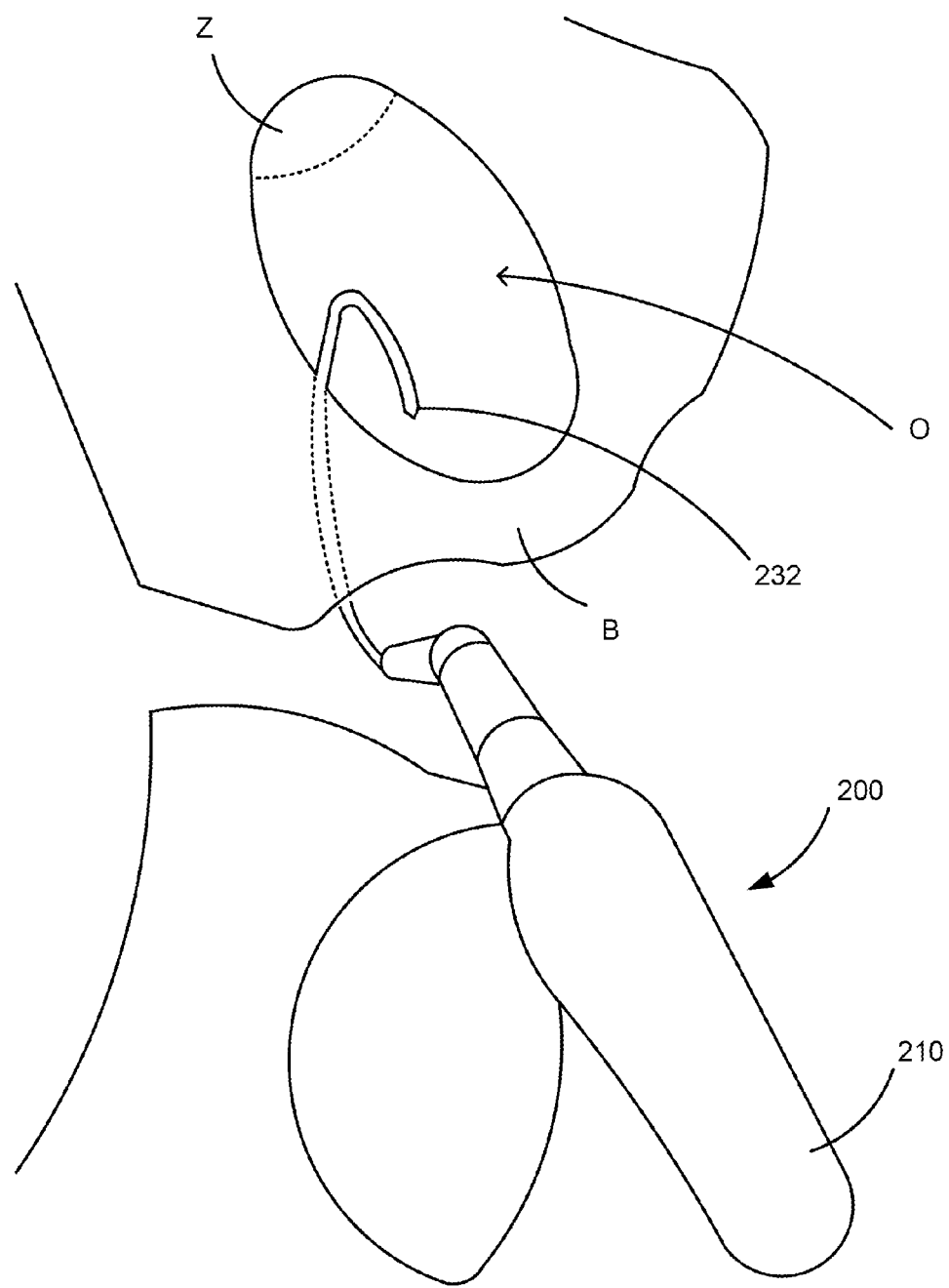

As illustrated in FIGS. 6 and 7, the physician may then insert the medical device 200 into the pelvic region of the patient (the implant is not illustrated in FIGS. 6 and 7). FIG. 6 is a side view of a portion of the pelvic region of a patient. FIG. 7 is a front view of a portion of the pelvic region of the patient. The distal end portion 230 of the medical device 200 is illustrated as being in its second position in FIG. 6 and is in its first position in FIG. 7. In one embodiment, the medical device 200 is inserted into the pelvic region of the patient through an anterior vaginal incision (not illustrated). In other embodiments, the medical device 200 is inserted into the pelvic region through another vaginal incision. In yet further embodiments, the distal end portion 230 is inserted into the body of the patient through another bodily incision.

In some embodiments, the medical device 200 is inserted into the body of the patient such that the distal tip 232 of the distal end portion 230 moves along an edge or in close proximity of an edge of a bone of the patient. In the illustrated embodiment, the medical device 200 is inserted into the body of the patient such that the distal tip 232 of the distal end portion 230 moves through bodily tissue T along an edge or a perimeter of a bone B that defines the obturator O of the patient (i.e., the ischio-pubic ramus bone). As pressure is kept on the medical device 200 during the insertion to move the medical device 200 within the body of the patient, the distal end portion 230 remains in its second position.

In some embodiments, as the medical device 200 is moved within the body such that the distal end portion 230 moves past or away from an edge of the bone B, the pressure or force on the distal end portion 230 is removed and the distal end portion 230 moves to its first position.

For example, as illustrated in FIGS. 6 and 7, the medical device 200 may be moved within the body of the patient until the distal end portion 230 of the medical device 200 moves past or away from an edge of the bone B. The physician may then pivot or move the proximal end portion 220 of the medical device 200 from position X to position Y by moving the proximal end portion 220 in the direction of arrow Z. As the proximal end portion 220 is moved to position Y, the pressure against the distal end portion 230 towards its second position is removed and the distal end portion 230 moves to its first position to continue to remain close or proximal to the edge or perimeter of the bone. Accordingly, the distal tip 232 is directed toward the obturator O (including the obturator muscles and membranes) of the patient. In some embodiments, as illustrated in FIG. 7, when the medical device 200 is disposed within the body of the patient and the distal end portion 230 is in its first position, the distal tip 232 is directed away from the nerves N, which are located proximal the obturator O of the patient.

Once the medical device 200 has advanced the implant to the desired location within the body of the patient, the implant can be decoupled from the medical device 200. The medical device 200 can be withdrawn from the body of the patient to leave the implant in place within the body of the patient.

In some embodiments, the medical device 200 or another insertion tool may be coupled to another portion of the implant to place the other portion of the implant into a location within the body of the patient. For example, the other portion of the implant may be inserted into the other obturator of the patient as described above with respect to the first portion of the implant. In some embodiments, the second portion of the implant is inserted into the body of the patient through the same incision through which the first portion of the implant was inserted.

Figure 8A:
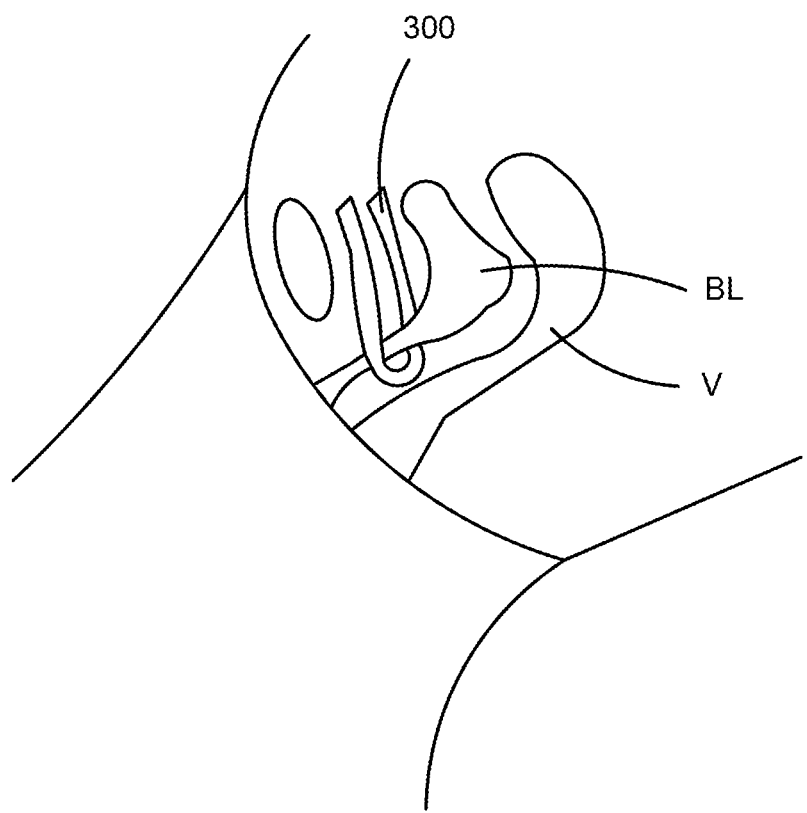
FIGS. 8A, 8B, and 8C schematically illustrates an implant disposed within a body of a patient.

In some embodiments, as schematically illustrated in FIG. 8A, the implant 300 is positioned between a portion of a vagina V of a patient and a portion of a bladder BL of the patient such that the implant 300 provides support to the bladder BL of the patient.

Figure 8B:
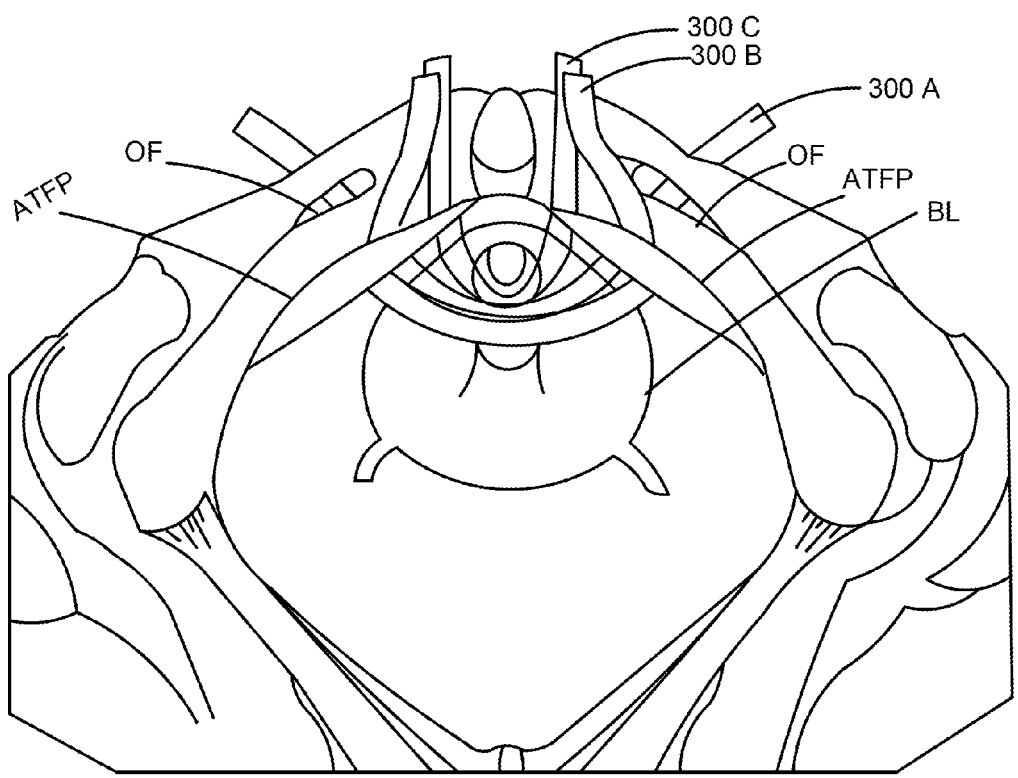

As illustrated in FIG. 8B, the implant may be positioned at different locations within the body of the patient. For example, as illustrated, implant 300A may be placed within the body of the patient such that the implant 300A extends through the obturator foramens OF of the patient. Alternatively, as illustrated, the implant 300B may extend between the ATFP (arcus tendineus facia pelvis) and the obturators of the patient. Alternatively, as illustrated, implant 300C may be disposed within the body of the patient in a "V" shape.

Figure 8C:
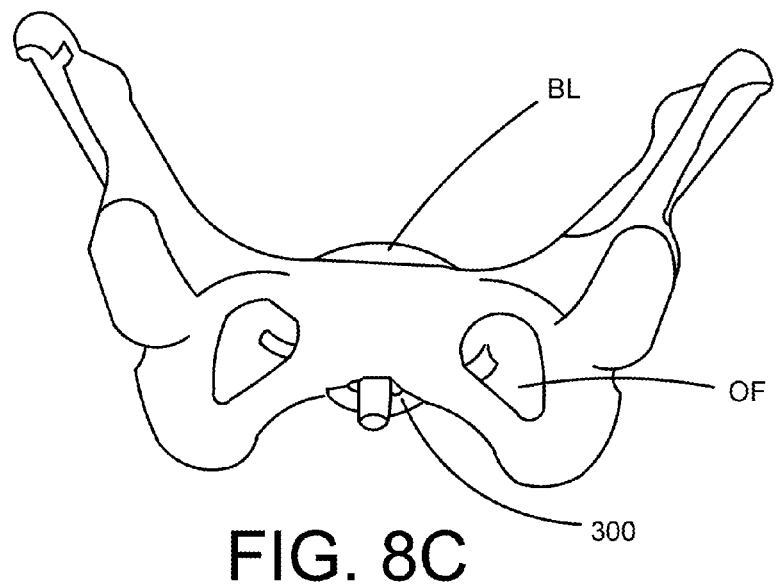

As illustrated in FIG. 8C, the implant 300 may be placed such that it extends toward the obturator foramens OF of the patient, but does not extend through the obturator foramens OF. For example, the implant 300 may be disposed within or coupled to muscles disposed proximate the obturator foramens OF.

Figure 9:
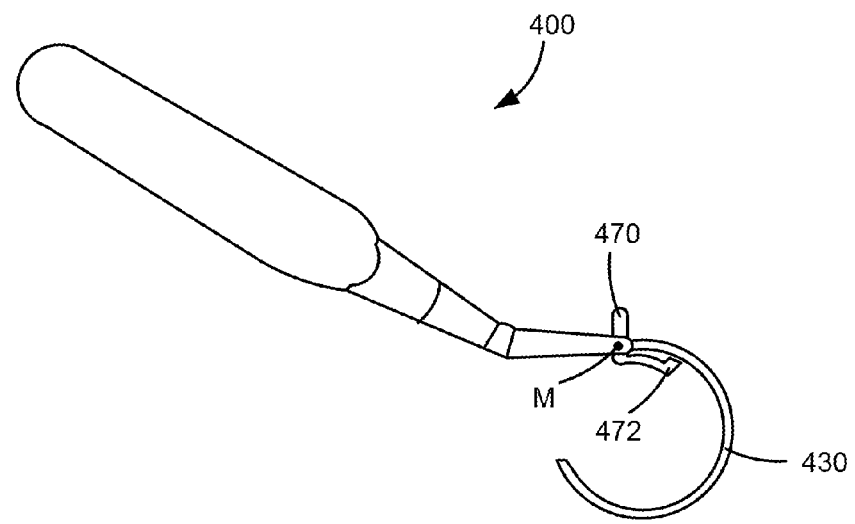
FIG. 9 illustrates a medical device according to an embodiment.

As illustrated in FIG. 9, in one embodiment, a medical device 400 includes a lever or actuator 470. In the illustrated embodiment, the lever or actuator 470 is pivotally coupled to a portion of the medical device 400 about axis M. Any known method of coupling may be used to pivotally couple the actuator 470 to a portion of the medical device 400. For example, a brad or a clip may be used to couple the actuator 470 to a portion of the medical device 400. A distal end portion 472 of the lever or actuator 470 is configured to contact or engage a distal end portion 430 of the medical device 400 to move the distal end portion 430 of the medical device to and from its various positions.

For example, in an embodiment in which the distal end portion 430 is biased to its first position, a physician may move the lever or actuator 470 to place or urge the distal end portion 430 into its second position. The distal end portion 430 may be coupled to an implant and placed within the body of the patient. The physician may then release the lever or actuator 470 to allow the distal end portion 430 to return to its first position.

In other embodiments, a portion of the proximal end portion of the medical device is configured to move with respect to the distal end portion to control or support the distal end portion of the medical device. For example, a portion of the proximal end portion, such as a handle portion, may move or slide along the medical device to urge the distal end portion into one of its positions (such as its second or non-biased position).

In other embodiments, the medical device has different shapes. For example, the curve of the distal end portion of the medical device may be different or have multiple curved portions. For example, the medical devices with distal end portions that include curves similar to the Obtryx®, Lynx®, and Advantage™ devices as sold by Boston Scientific Corporation may be used.

Figure 10:
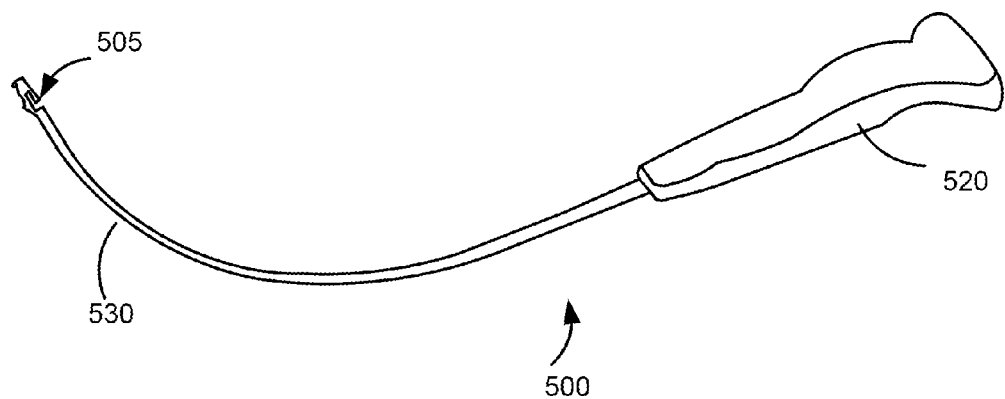
FIGS. 10-13 illustrate medical devices according to an embodiment.
Figure 11:
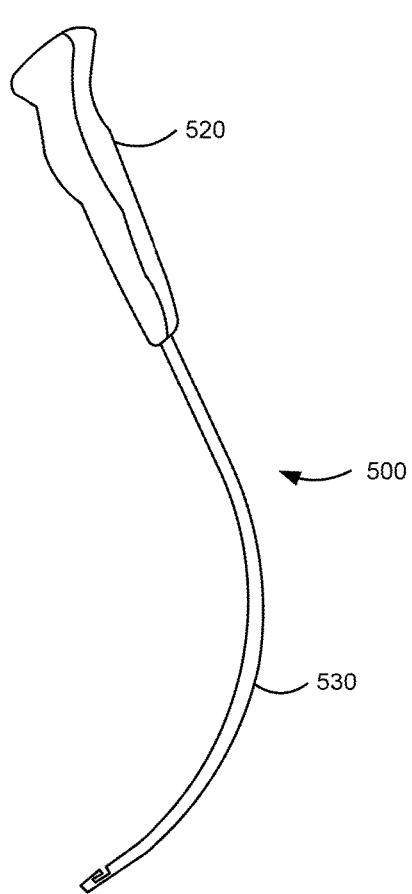
Figure 12:
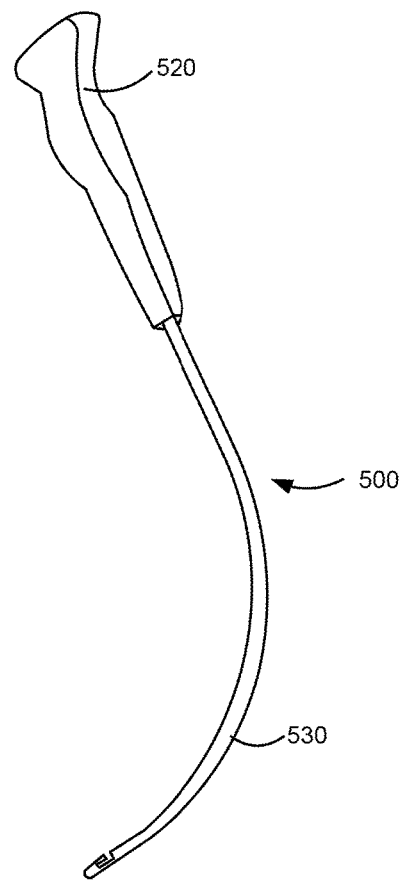

FIGS. 10-12 illustrate a medical device 500 according to an embodiment. The medical device 500 includes a proximal end portion 520 and a distal end portion 530. The distal end portion 530 is configured to move or flex with respect to the proximal end portion 520. Specifically, the distal end portion 530 may be placed in a first position (FIG. 10), a second position (FIG. 11), and a third position (FIG. 12) with respect to the proximal end portion 510. Specifically, in this embodiment, the distal end portion 530 of the medical device 500 is most linear when then distal end portion 530 is in its first position and is most curved when the distal end portion 530 is in its second position.

In the illustrated embodiment, the medical device 500 includes a coupling portion 505 configured to couple the medical device to a bodily implant. In some embodiments, the medical device 500 may be used to deliver or insert the implant into a body of a patient. In some embodiments, the medical device 500 may be used to deliver an implant to the pelvic region of the patient via a retropubic (below) or a suprapubic (above) approach.

Figure 13:
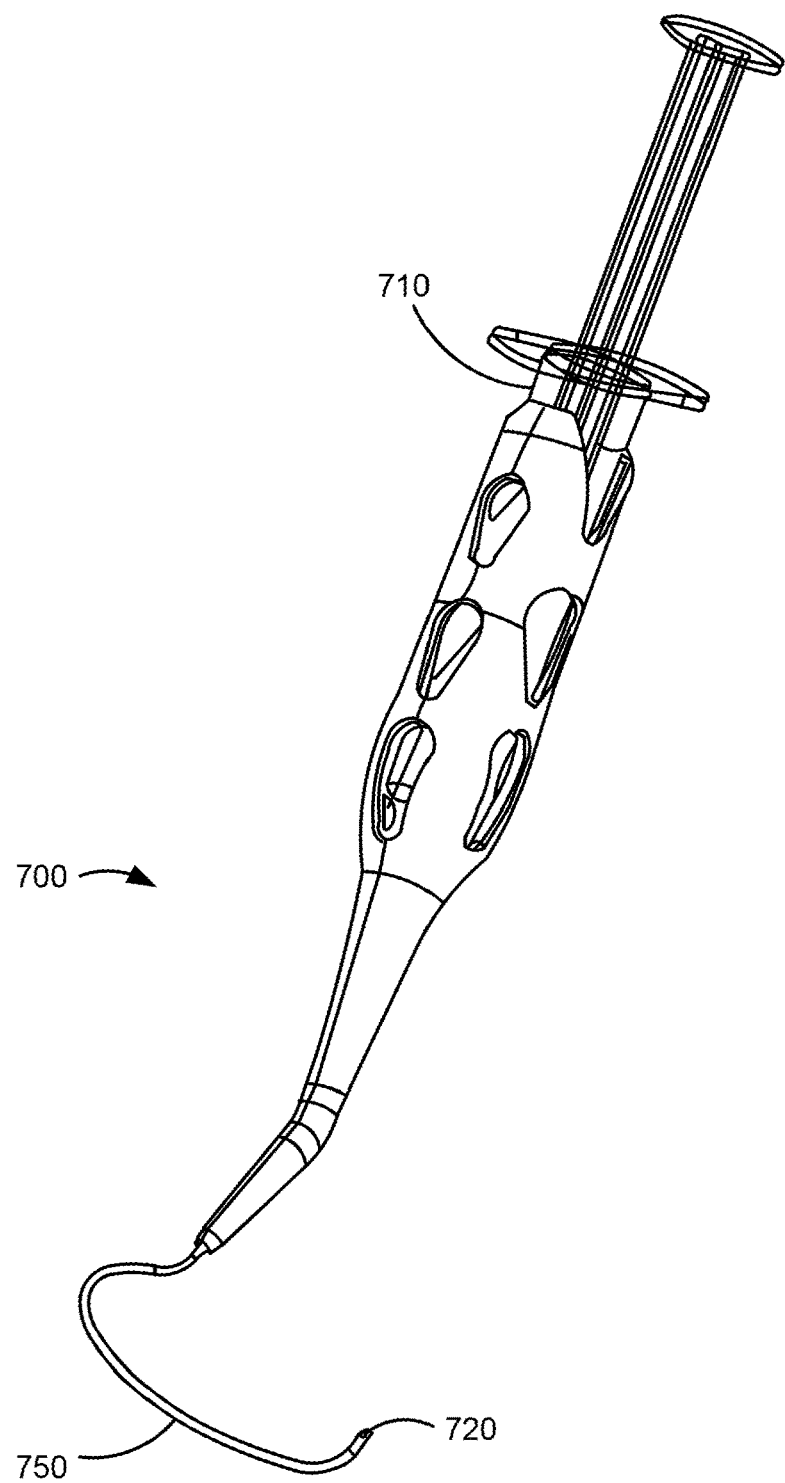

FIG. 13 illustrates another medical device 700 according to an embodiment. The medical device 700 includes a syringe 710 and defines a lumen 720 that extends through the medical device 700. Thus, in such embodiments, a liquid, such as a medication or an anesthetic may be inserted into the patient as the medical device 700 is advanced within the body of the patient. The distal end portion 750 of the medical device 700 is configured to bend or flex into a plurality of positions. In some embodiments, the syringe 710 is a 20 cc syringe. In other embodiments, the syringe 710 is larger or smaller than 20 cc.

Figure 14:
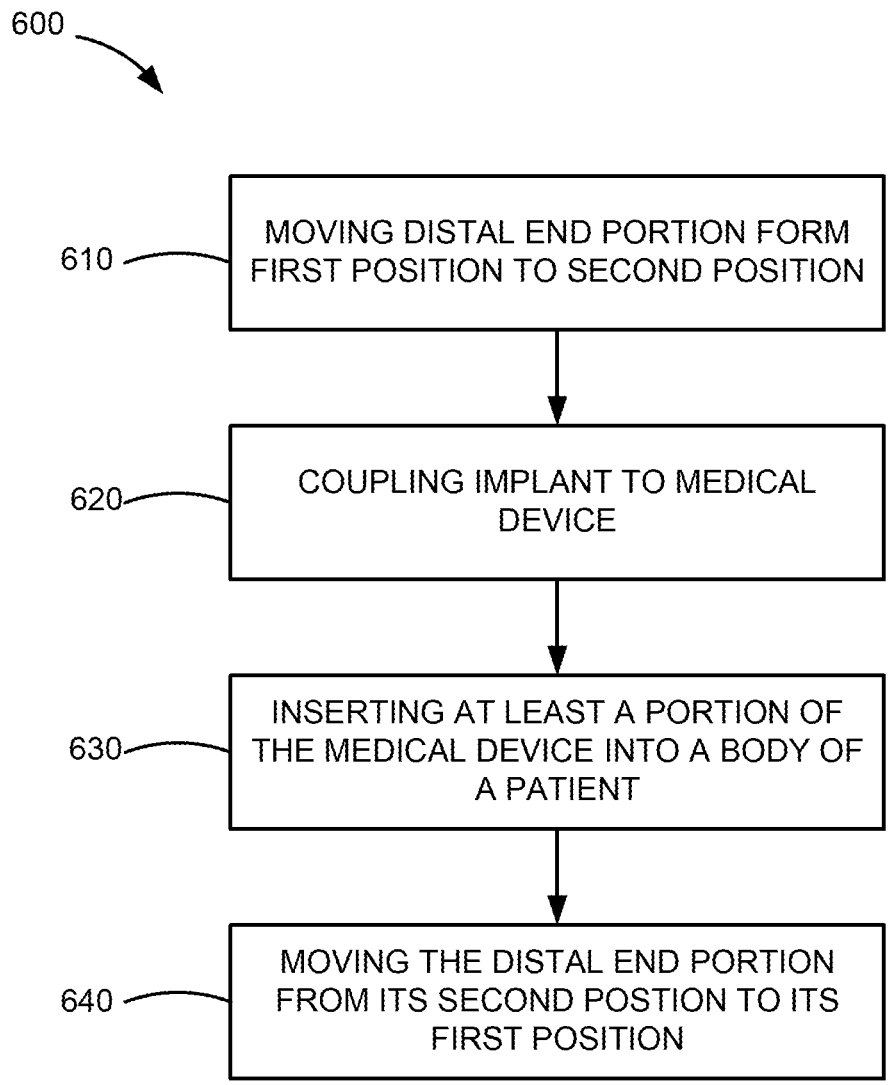
FIG. 14 is a flow chart of a method of inserting an implant into a body of a patient according to an embodiment.

In some embodiments, as illustrated in FIG. 14, a method 600 of implanting a bodily implant includes, at step 610, moving a distal end portion of a medical device from a first position to a second position. The moving may include moving the distal end portion of the medical device with a hand of the physician. In some embodiments, the moving includes activating a lever or actuator to move the distal end portion from its first position to its second position.

At step 620, the method includes coupling an implant to the medical device. In some embodiments, the coupling includes treading a portion of the medical implant through a slot defined by the medical device.

At step 630, the method includes inserting at least a portion of the medical device into a body of a patient. In some embodiments, the inserting includes making a vaginal incision (such as an anterior vaginal incision) and inserting at least a portion of the medical device into the body of the patient.

At step 640, the method includes moving the distal end portion of the medical device from the second position to the first position. In some embodiments, the moving includes moving the distal end portion of the medical device from the second position to the first position while the distal end portion is disposed within the body of the patient. In some embodiments, the moving includes moving a proximal end portion of the medical device with respect to the body of the patient.

In some embodiment, the coupling of step 620 occurs after the moving of step 640. In other words, in some embodiments, the medical device may be inserted and placed within the body of the patient. Then the implant may be coupled to the medical device. In such embodiments, the medical device may then be retraced from the body of the patient to position the implant within the body of the patient.

In some embodiments, the method includes moving the medical device within the body of the patient after moving the distal end portion of the medical device from the second position to the first position.

In some embodiments, a medical device includes an elongate member having a proximal end portion and a distal end portion. The distal end portion is configured to be inserted into a body of a patient. The elongate member is configured to be associated with a bodily implant. The distal end portion of the elongate member is configured to move from a first position to a second position such that the distal end potion of the elongate member may be inserted into the body of the patient in its second position and is moved to its first position while disposed within the body of the patient.

In some embodiments, the distal end portion is configured to flex from its first portion to its second position. In some embodiment, the proximal end portion of the elongate member includes a handle. In some embodiments, the elongate member includes a coupler configured to associate the elongate member with the bodily implant. In some embodiments, the distal end portion of the elongate member defines a slot configured to associate the elongate member with the bodily implant. In some embodiments, the distal end portion of the elongate member defines an L shaped slot configured to associate the elongate member with the bodily implant. In some embodiments, the distal end portion of the elongate member defines a T shaped slot configured to associate the elongate member with the bodily implant.

In some embodiments, the distal end portion of the elongate member includes a curve having a first radius of curvature when the distal end portion is in its first position. The distal end portion of the elongate member includes a curve having a second radius of curvature when the distal end portion is its second position. The second radius of curvature is larger than the first radius of curvature.

In some embodiments, the distal end portion of the elongate member includes a curve having a first radius of curvature when the distal end portion is in its first position. The distal end portion of the elongate member includes a curve having a second radius of curvature when the distal end portion is its second position. The second radius of curvature is larger than the first radius of curvature. The distal end portion of the elongate member is biased to its first position.

In some embodiments, the medical device includes an actuator coupled to the elongate member and being configured to move the distal end portion of the elongate member from its first position to its second position.

In some embodiments, the medical device includes an actuator coupled to the elongate member and being configured to move the distal end portion of the elongate member from its first position to its second position. The actuator is configured to be disposed outside of a body of a patient when the distal end portion of the elongate member is disposed within the body of the patient.

In some embodiments, a kit includes a medical device and an implant. The medical device has an elongate member having a proximal end portion and a distal end portion. The distal end portion is configured to be inserted into a body of a patient. The distal end portion of the elongate member is configured to move from a first position to a second position prior to placement of the distal end portion into a body of a patient. The distal end portion of the elongate member is configured to move from the second position to the first position while the distal end portion of the elongate member is disposed within the body of the patient. The implant is configured to be inserted into the body of the patient. The medical device is configured to be associated with the implant and is configured to help place the implant within the body of the patient.

In some embodiments, the distal end portion of the elongate member defines a slot configured to associate the elongate member with the bodily implant. In some embodiments, the distal end portion of the elongate member includes a curve having a first radius of curvature when the distal end portion is in its first position. The distal end portion of the elongate member includes a curve having a second radius of curvature when the distal end portion is its second position. The second radius of curvature is larger than the first radius of curvature.

In some embodiments, the distal end portion of the elongate member includes a curve having a first radius of curvature when the distal end portion is in its first position. The distal end portion of the elongate member includes a curve having a second radius of curvature when the distal end portion is its second position. The second radius of curvature is larger than the first radius of curvature. The distal end portion of the elongate member is biased to its first position.

In some embodiments, the elongate member includes an actuator configured to move the distal end portion of the elongate member from its first position to its second position.

In some embodiments, a method includes (1) moving a distal end portion of a medical device from a first position to a second position, (2) inserting at least a portion of the medical device into a body of a patient, and (3) moving the distal end portion of the medical device from the second position to the first position.

In some embodiments, the method includes moving the medical device within the body of the patient after moving the distal end portion of the medical device from the second position to the first position. In some embodiments, the method includes coupling a bodily implant to the medical device.

In some embodiments, the moving the distal end portion of the medical device from the second position to the first position includes moving a proximal end portion of the medical device with respect to the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
an elongate member having a proximal end portion and a distal end portion, the distal end portion being configured to be inserted into a body of a patient, the distal end portion including a curved portion, the curved portion having a distal tip, the elongate member including a handle and a tapered portion extending from the handle, the handle including a portion configured to be grasped by a physician, the tapered portion being disposed between the curved portion and the handle, the tapered portion having a longitudinal axis, the longitudinal axis of the tapered portion being disposed at a non-zero angle with respect to a longitudinal axis of the handle, the tapered portion extending in a direction away from the longitudinal axis of the handle, the curved portion including a portion that directly extends from the tapered portion and curves toward the longitudinal axis of the handle,
the curved portion including a slot configured to associate the elongate member with a bodily implant, the curved portion being configured to move from a first position to a second position such that the distal end portion of the elongate member can be inserted into the body of the patient in the second position and moved to the first position while disposed within the body of the patient, the curved portion having a first radius of curvature when in the first position, the curved portion having a second radius of curvature different than the first radius of curvature when in the second position; and an actuator movably coupled directly to the tapered portion, wherein actuation of the actuator applies a force on the curved portion such that the curved portion is moved to the second position, the curved portion being disposed distally from the actuator.

2. The medical device of claim 1, wherein the curved portion is configured to flex from the first position to the second position.

3. The medical device of claim 1, wherein the curved portion includes a stainless steel material.

4. The medical device of claim 1, wherein the curved portion has a first end portion extending from the tapered portion, and a second end portion having the distal tip, wherein the first end portion and the second end portion are disposed on opposite sides of the longitudinal axis of the handle regardless of whether the curved portion is in the first position or the second position.

5. The medical device of claim 1, wherein the slot includes an L shaped slot.

6. The medical device of claim 1, wherein the slot includes a T shaped slot.

7. The medical device of claim 1, wherein the second radius of curvature is larger than the first radius of curvature.

8. The medical device of claim 1, wherein the curved portion is biased to the first position.

9. The medical device of claim 1, wherein the actuator includes a lever pivotally coupled directly to the tapered portion, the lever including an end portion configured to apply pressure to the curved portion to move the curved portion to the second position.

10. The medical device of claim 1, wherein the distal tip includes a sharp portion configured to pierce bodily tissue.

11. A kit, comprising:
a medical device having an elongate member, the elongate member having a distal end portion, the distal end portion configured to be inserted into a body of a patient, the distal end portion including a curved portion, the curved portion having a slot and a distal tip, the elongate member including a handle and a tapered portion distally extending from the handle, the handle configured to be grasped by a physician, the curved portion distally extending from the tapered portion, the tapered portion having a longitudinal axis, the longitudinal axis of the tapered portion being disposed at a non-zero angle with respect to a longitudinal axis of the handle, the tapered portion extending in a direction away from the longitudinal axis of the handle, the curved portion including a portion that directly extends from the tapered portion and curves toward the longitudinal axis of the handle,
the curved portion being configured to move from a first position to a second position prior to placement of the distal end portion into the body of the patient, the curved portion being configured to move from the second position to the first position while the distal end portion of the elongate member is disposed within the body of the patient, wherein the curved portion has a first radius of curvature when in the first position, wherein the curved portion has a second radius of curvature larger than the first radius of curvature when the in the second position, the curved portion being biased to the first position,
the medical device including an actuator movably coupled directly to the tapered portion, wherein actuation of the actuator applies a force on the curved portion such that the curved portion bends to the second position, the curved portion being disposed distally from the actuator; and
an implant being configured to be inserted into the body of the patient, the implant configured to be coupled to the slot of the curved portion.

12. The kit of claim 11, wherein the implant includes a mesh material.

13. The kit of claim 12, wherein the mesh material includes tangs to help retain the implant within the body of the patient.

14. The kit of claim 11, wherein the curved portion includes a first end portion extending from the tapered portion, and a second end portion having the distal tip, wherein the actuator includes a lever pivotally coupled directly to the tapered portion, the lever including an end portion configured to apply pressure to the first end portion to move the curved portion to the second position.

15. A method, comprising:
moving a distal end portion of a medical device from a first position to a second position, the distal end portion including a curved portion coupled to a handle of the medical device, the curved portion having a first radius of curvature when the distal end portion is in the first position, the curved portion having a second radius of curvature larger than the first radius of curvature when the distal end portion is in the second position, the curved portion being biased to the first position;
inserting at least a portion of the medical device into a body of a patient while the curved portion is in the second position such that a distal tip of the distal end portion moves through bodily tissue along an edge or a perimeter of a bone that defines an obturator of the patient; and
moving the handle of the medical device, wherein as the handle is moved, pressure against the distal end portion is removed causing the curved portion to return to the first position such that the distal tip is directed away from nerves located proximate to the obturator of the patient.

16. The method of claim 15, further comprising:
moving the medical device within the body of the patient after the curved portion is returned to the first position.

17. The method of claim 15, further comprising:
coupling a bodily implant to the medical device.

18. The method of claim 15, wherein the medical device includes a lever disposed on a portion of the medical device apart from the handle of the medical device, the lever configured to pivot thereby engaging the distal end portion such that the distal end portion is moved from the first position to the second position.

* * * * *